United States Patent
Bajac et al.

(10) Patent No.: US 10,485,966 B2
(45) Date of Patent: Nov. 26, 2019

(54) MEDICAL CONNECTOR

(71) Applicant: GVS S.P.A., Zola Predosa (BO) (IT)

(72) Inventors: Joao Bajac, Sao Caetano do Sul (BR); Carlos Henrique Alvarez, Indaiatuba (BR)

(73) Assignee: GVS S.P.A., Zola Predosa (BO) (IT)

( * ) Notice: Subject to any disclaimer, the term of this patent is extended or adjusted under 35 U.S.C. 154(b) by 152 days.

(21) Appl. No.: 15/737,879

(22) PCT Filed: Jun. 30, 2016

(86) PCT No.: PCT/IB2016/053921
§ 371 (c)(1),
(2) Date: Dec. 19, 2017

(87) PCT Pub. No.: WO2017/002058
PCT Pub. Date: Jan. 5, 2017

(65) Prior Publication Data
US 2018/0229018 A1    Aug. 16, 2018

(30) Foreign Application Priority Data

Jul. 2, 2015  (IT) .............................. UB2015A1860

(51) Int. Cl.
*A61M 39/10* (2006.01)
*A61M 39/26* (2006.01)
A61M 39/24 (2006.01)

(52) U.S. Cl.
CPC ............ *A61M 39/10* (2013.01); *A61M 39/26* (2013.01); *A61M 2039/1033* (2013.01); *A61M 2039/1072* (2013.01); *A61M 2039/2426* (2013.01)

(58) Field of Classification Search
CPC .... A61M 39/14; A61M 39/26; A61M 39/143; A61M 39/10
See application file for complete search history.

(56) References Cited

U.S. PATENT DOCUMENTS 6,050,978 A * 4/2000 Orr ................ A61M 39/26
251/149.1
6,079,432 A * 6/2000 Paradis ............. A61M 39/26
137/1

(Continued)

FOREIGN PATENT DOCUMENTS

EP    2123322 A2   11/2009
EP    2865410 A1    4/2015

(Continued)

OTHER PUBLICATIONS

International Search Report and Written Opinion dated Jun. 6, 2016 for PCT/IB2016/053921 to GVS S.P.A. filed Jun. 30, 2016.

*Primary Examiner* — Imani N Hayman
*Assistant Examiner* — Tiffany Legette
(74) *Attorney, Agent, or Firm* — Vorys, Sator, Seymour and Pease LLP

(57) ABSTRACT

A medical connector including a first rigid body capable of being connected to a medical infusion line and having an elongated tubular element in which there is a conduit opening out at opposite extremities, a first extremity of the tubular element being capable of being directly connected to the medical infusion line, the elongated tubular element being capable of being closed off at one of its first open extremities by a second body associated with the first body. The second body is of yielding material and at least partly covers the elongated element and extends beyond the second extremity of that element in such a way as to close off the opening thereof, such second body being overmoulded onto the first body and forming a single piece therewith.

18 Claims, 2 Drawing Sheets

(56) References Cited

U.S. PATENT DOCUMENTS

| | | |
|---|---|---|
| 2008/0093571 A1 | 4/2008 | Desecki |
| 2008/0103482 A1* | 5/2008 | Fangrow .............. A61M 39/10 604/523 |
| 2008/0172003 A1 | 7/2008 | Plishka et al. |
| 2008/0287920 A1 | 11/2008 | Fangrow et al. |
| 2010/0108681 A1 | 5/2010 | Jepson et al. |
| 2011/0130717 A1 | 6/2011 | David et al. |

FOREIGN PATENT DOCUMENTS

| | | |
|---|---|---|
| WO | 2008048777 A2 | 4/2008 |
| WO | 2009144583 A1 | 12/2009 |

* cited by examiner

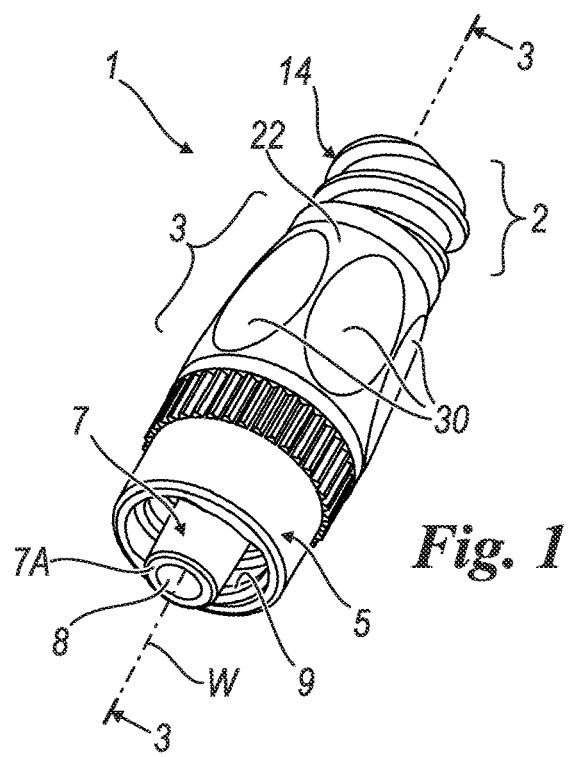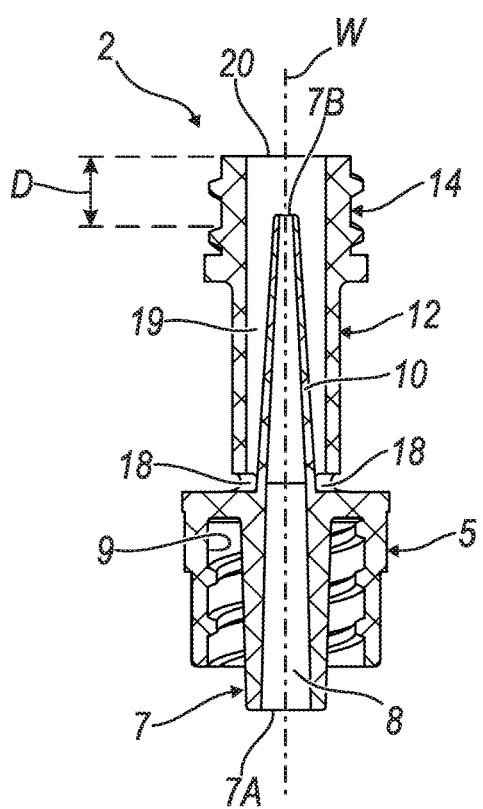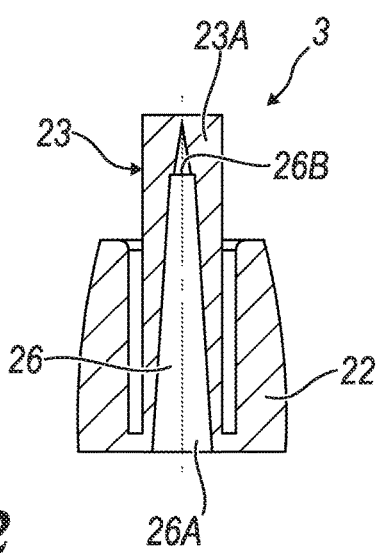
Fig. 1
Fig. 2

MEDICAL CONNECTOR

CROSS-REFERENCE TO RELATED APPLICATIONS

This is a § 371 National Stage Application of International Application No. PCT/IB2016/053921 filed on Jun. 30, 2016, claiming the priority of Italian Patent Application No. UB2015A001860 filed on Jul. 2, 2015.

This invention relates to a medical connector according to the precharacterising clause of the principal claim.

As is known, in a medical infusion line a tubular member or connector, which is for example "Y"-shaped, through which a drug can be introduced into that line, is frequently provided. For this purpose a plug of yielding material which can be perforated by the needle of a syringe for introducing a drug into the line is placed on one tubular branch of such connector.

This solution therefore provides for the use of a syringe fitted with a needle, something which may also result in contact between it and an operator, with obvious disadvantages. In addition to this the needle may break inside the yielding plug, something which would mean that the entire connector has to be replaced. In addition to this there is also the need to provide for the disposal of used needles, an operation requiring care and attention, which if not performed may result in punctures and corresponding risks for operators involved in disposal.

US 2008/287920 describes a medical connector having the characteristics indicated in the precharacterising part of claim 1. This document describes a medical connector having a first rigid body capable of being connected to a medical infusion line; the rigid body has a tubular portion in which there is a conduit which can be closed off at one extremity by a second body of yielding material which is overmoulded onto the first rigid body. In particular it is described that this second body closes off the extremity of such conduit and is also inserted into the conduit itself. Only a portion of the second body is placed above a corresponding extremity of the tubular portion of the first body.

The yielding body does not enclose such first body and in use, after the medical connector has been detached from the needle of a syringe or a normal Luer connector, such yielding material may come out of the conduit of the tubular portion or even become detached from it. This could expose a medical operator to contact with the medical product present in the connector, a product which could also be toxic to that operator (such as for example a product used in the treatment of cancer).

US 2010/0108681 describes a connection device which can act together with a medical connector without a needle in which such device comprises an axially mobile perforating member.

US 2008/0093571 describes a device activated by a Luer connector comprising a first body having an internal conduit closed off at one extremity by a second body of yielding material capable of acting together with a male Luer connector. This solution has the same disadvantages as described in connection with US 2008/287920 cited above.

WO 2008/048777 describes a medical connector activated by a Luer connector and comprising an elongated body with an internal through conduit which is closed off at one extremity by a resilient element within the medical connector.

This solution also has the disadvantages described for US 2008/287920.

The object of this invention is to provide a medical connector which can receive a fluid from a syringe without the latter having to be provided with a needle.

Another object is to provide an improved medical connector which does not need to be assembled, but which nevertheless comprises two materials, one rigid and one yielding.

Another object is to provide a medical connector of the type mentioned which has low cost and is simple to use.

Another object is to provide a medical connector having a plurality of parts connected together in such a way that they are not able to separate and thus form a single-piece body so as to offer high safety during use to medical operators using it, as well as during emergency actions requiring fast times for connecting the connector to the components of a medical infusion line.

These and other objects which will be obvious to those skilled in the art are accomplished by a medical connector according to the appended claims.

For a better understanding of this invention the following drawings are appended purely by way of example, but without being limiting, in which:

FIG. 1 shows a perspective view of a connector according to the invention from a first angle;

FIG. 2 shows a view in longitudinal cross-section of two components defining the connector in FIG. 1 arranged side by side;

Figure 3:
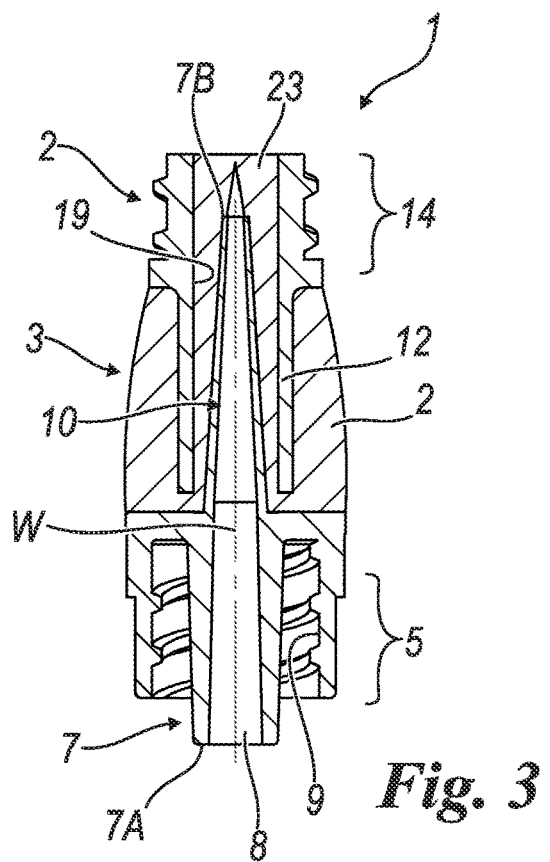
FIG. 3 shows a view in cross-section along the line 3-3 in FIG. 1.
Figure 4:
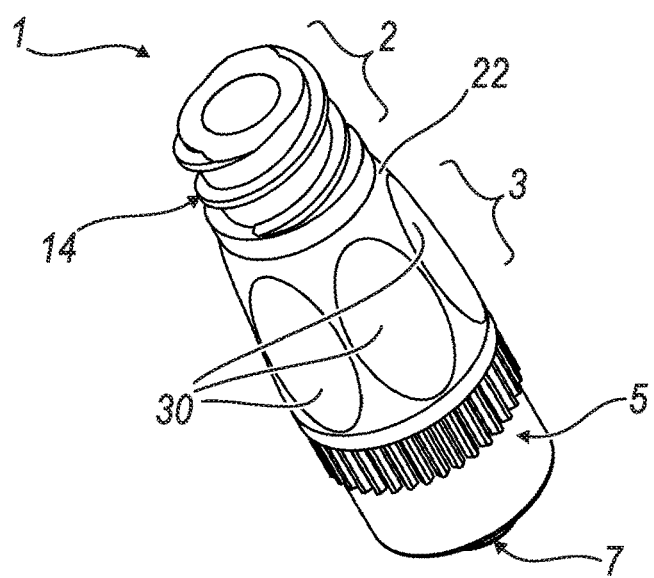
FIG. 4 shows a perspective view of the connector in FIG. 1 from another angle.

With reference to the figures mentioned, a medical connector according to the invention is generically indicated by 1. This comprises two components or main bodies, 2 and 3, which are made of materials having different rigidities; the first component or body 2 is rigid (for example it is of polycarbonate, ABS, PVC and similar rigid materials), while the second 3 is of a yielding material (such as silicone, TPE or the like). This second body or component is overmoulded onto first body 2 and forms a single piece therewith. In FIG. 2 these bodies are shown side by side in order to aid description.

First body 2, which is itself of one piece, has a first extremity portion 5, in the form of a cup and arranged around an inner tubular element 7 having a central conduit 8 located along the axis W of the first body. An inner wall 9 of cup portion 5 is threaded and is able to act together with a normal male Luer connector of a medical line or other medical device having such a connector (not shown).

Through a part 10, tubular element 7 continues within an intermediate portion 12 of first body or component 2 and ends in the second extremity portion 14 of aforesaid body 2. This second extremity portion 14 is externally threaded and is able to act together with a female Luer connector of a syringe without a needle (not shown), which is in itself known.

Part 10 of tubular element 7 is of frustoconical shape. Central conduit 8 of said element 7 opens at extremities 7A and 7B of the latter which respectively correspond to the first and second portions 5 and 14 of body 2. In particular first extremity 7A of element 7 is external to first extremity portion 5 of body 2, while second extremity 7B is internal to abovementioned secondary extremity portion 14.

Between first extremity portion 5 and intermediate portion 12 there is at least one opening and preferably a plurality of openings 18 opening between a space 19 existing around part 10 of tubular element 7 or between this and the wall of the intermediate portion and extremity portions 12 and 14 of body 2. It should be noted that second extremity 7B of the tubular element terminates at a distance D from an opening 20 in second extremity portion 14 of body 2 into which space 19 opens. Through this or such openings the soft material defining the second body is overmoulded onto element 7.

Second body or component 3, whose shape is illustrated individually in FIG. 2, is capable of being overmoulded in space 19 and around intermediate portion 12 of body 2. This second component has a first outer portion 22 which can be placed on the outside of second extremity portion 14 and a second portion 23, attached to first portion 22, capable of being located in space 19 above second extremity 7B of tubular element 7, closing off the opening. This second portion nevertheless remains within second extremity portion 14 of body 2. The connection between first portion 22 and second 23 takes place thanks to the soft and yielding material of second body 3 which penetrates and stops within each opening 18 of body 2. This body 3 is therefore a single component (with its portions 22 and 23) enclosing portion 12.

It should be noted that second portion 23 has an internal cavity 26 opening into its first extremity 26A and closed off at its second extremity 23B. When body 3 is overmoulded onto part 10 of tubular element 7 cavity 26 has a shape matching that of that element.

Internal cavity 26 is instead closed off at its other extremity 26B by a yielding extremity part 23A of second portion 23. This yielding part 23A can split when a syringe without a needle (but having a usual projecting extremity tubular portion) is connected to the second extremity portion 14 of first body or component 2.

It is intended in fact that connector 1 should be connected (as in FIG. 1) to a medical line (not shown) through the first extremity portion 5 of first body 2. In this the syringe without a needle is screwed onto second extremity portion 14 of such body 2. In doing this the normal tubular portion of such syringe "parts" yielding extremity part 23A of second portion 23 and can come into contact with extremity 7B of tubular element 7 connecting to it.

The displaced yielding part seals against the syringe and the tubular element in contact and allows whatever is present in the syringe (for example medical fluid) to be transferred to the latter. When the syringe is separated from connector 1 the resilience of the yielding part seals off tubular element 7.

The solution described therefore relates to a medical connector having two components 2 and 3, the first rigid and the second, of soft and yielding material, being overmoulded onto the first body. This allows for a syringe without a needle to be used to transfer a fluid in a medical line. Safer use by the part of a user of the syringe, for example a nurse, and even safer insertion of that fluid into the medical line is achieved as a consequence.

The connector is also of a single piece and is made in such a way as to close off automatically after being connected to a syringe; in addition to this first portion 22 may be shaped with lowered parts 30 to assist attachment of the connector and its connection to the syringe and/or the medical line.

As a result of the shape in which it is constructed component 3 encloses first component or body 2 and is stably associated therewith, with the impossibility of second body or component 3 becoming detached from the first. This is due to the presence of the connection between portion 22 and 23 of that second body defined by the material of body 3 placed within each opening 18 of body 2.

A preferred embodiment of the invention and its use has been described. Other embodiments and uses are possible, such as that which provides for connector 1 to be associated through second extremity 7B of first body 2 with a branch of a normal X or Y connector, part 7B being nevertheless able to act together with a syringe without a needle to introduce fluids into the X or Y-shaped connector. These variants are also to be understood to fall within the scope of this invention as defined by the appended claims.

The invention claimed is:

1. A medical connector comprising: a first rigid body and a second body, the first rigid body having an elongated tubular element comprising a conduit having a first open extremity and a second open extremity opposite the first open extremity, the first open extremity of the elongated tubular element configured to be directly connected to a medical infusion line, the second open extremity being configured to be covered and closed off by the second body, the second body being of a yielding material and having a first portion and a second portion, wherein the first portion surrounds the second portion, the first rigid body having a first extremity portion having an internal threaded portion connecting the medical infusion line to the first open extremity and a second extremity portion having an external threaded portion configured to connect to a needleless syringe or other medical device having a female Luer connector, wherein the second body is configured to extend beyond the second open extremity to close off the second open extremity, the first rigid body having an intermediate portion that is located between the first extremity portion and the second extremity portion, a portion of the elongated tubular element including the second open extremity being surrounded by the intermediate portion such that a space is defined between the portion of the elongated tubular element and the intermediate portion, the second portion of the second body configured to be positioned within the space when the first portion of the second body is positioned around the intermediate portion.

2. The connector according to claim 1, wherein the first portion of the second body has a gripping portion to assist attachment.

3. The connector according to claim 1, wherein at least one opening is located between the first extremity portion and the intermediate portion, wherein the at least one opening is configured to receive the yielding material to form the second body.

4. The medical connector according to claim 1, wherein the first extremity portion has a cup-shaped portion and the internal threaded portion is provided on an inner wall of the cup-shaped portion, the first open extremity of the tubular element being located within the cup-shaped portion.

5. The medical connector according to claim 1, wherein the second open extremity of the tubular element within the second extremity portion such that the second portion is configured to overlap the second open extremity of the tubular element located inside the second extremity portion.

6. The medical connector according to claim 1, wherein the first extremity portion has a cup-shaped portion and the internal threaded portion is provided on an inner wall of the cup-shaped portion, the first open extremity located within the cup-shaped portion, the second open extremity being located within the second extremity portion, such that the second portion of the second body is configured to overlap the second open extremity located inside the second extremity portion.

7. The connector according to claim 6, wherein the first open extremity projects proximally from the first extremity portion of the first body.

8. The medical connector according to claim 1, wherein the second portion of the second body configured to cover the second open extremity is frustoconical in shape.

9. The medical connector according to claim 8, wherein the portion of the elongated tubular element configured to be positioned in the space is frustoconical and includes the second open extremity.

10. The medical connector according to claim 1, wherein the second body being of yielding material is configured to be overmoulded onto the first rigid body to form a single piece therewith.

11. The connector according to claim 10, wherein the first portion of the second body has a gripping portion to assist attachment.

12. The connector according to claim 10, wherein at least one opening is located between the first extremity portion and the intermediate portion, wherein the at least one opening is configured to receive the yielding material to form the second body.

13. The medical connector according to claim 10, wherein the first extremity portion has a cup-shaped portion and the internal threaded portion is provided on an inner wall of the cup-shaped portion, the first open extremity of the tubular element being located within the cup-shaped portion.

14. The medical connector according to claim 10, wherein the second open extremity of the tubular element within the second extremity portion such that the second portion is configured to overlap—the second open extremity of the tubular element located inside the second extremity portion.

15. The medical connector according to claim 10, wherein the second portion of the second body configured to cover—the second open extremity is frustoconical in shape.

16. The medical connector according to claim 15, wherein the portion of the elongated tubular element configured to be positioned in the space is frustoconical and includes the second open extremity.

17. The medical connector according to claim 10, wherein the first extremity portion has a cup-shaped portion and the internal threaded portion is provided on an inner wall of the cup-shaped portion, the first open extremity located within the cup-shaped portion, the second open extremity being located within the second extremity portion, such that the second portion of the second body is configured to overlap the second open extremity located inside the second extremity portion.

18. The connector according to claim 17, wherein the first open extremity projects proximally from the first extremity portion of the first body.

* * * * *